(12) United States Patent
Matsumoto et al.

(10) Patent No.: US 7,687,138 B2
(45) Date of Patent: *Mar. 30, 2010

(54) POROUS CALCIUM PHOSPHATE CERAMIC AND METHOD FOR PRODUCING SAME

(75) Inventors: Toshio Matsumoto, Tokyo (JP); Masanori Nakasu, Tokyo (JP)

(73) Assignee: Hoya Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/577,426

(22) PCT Filed: Oct. 27, 2004

(86) PCT No.: PCT/JP2004/015941

§ 371 (c)(1),
(2), (4) Date: Apr. 27, 2006

(87) PCT Pub. No.: WO2005/039544

PCT Pub. Date: May 6, 2005

(65) Prior Publication Data

US 2007/0072009 A1    Mar. 29, 2007

(30) Foreign Application Priority Data

Oct. 27, 2003  (JP) .............................. 2003-366404

(51) Int. Cl.
  *B32B 3/26* (2006.01)
  *A61F 2/28* (2006.01)

(52) U.S. Cl. .............. 428/316.6; 428/315.7; 428/312.2; 428/306.6; 428/307.3; 428/307.7; 623/23.56; 623/23.5; 623/23.76

(58) Field of Classification Search ............. 428/319.1, 428/306.6, 307.3, 307.7, 316.6, 312.2; 623/23.56, 623/23.5, 23.76

See application file for complete search history.

(56) References Cited

U.S. PATENT DOCUMENTS

| 4,626,392 | A  | * | 12/1986 | Kondo et al. ................. 264/643 |
| 6,340,648 | B1 |   | 1/2002  | Imura et al. |
| 6,426,114 | B1 | * | 7/2002  | Troczynski et al. ........ 427/2.27 |
| 2002/0114938 | A1 |   | 8/2002 | Matsumoto |
| 2003/0152606 | A1 |   | 8/2003 | Gerber |
| 2004/0153165 | A1 |   | 8/2004 | Li et al. |
| 2004/0185181 | A1 |   | 9/2004 | Matsumoto |
| 2005/0031704 | A1 | * | 2/2005 | Ahn ........................... 424/602 |
| 2005/0049715 | A1 | * | 3/2005 | Ito et al. ...................... 623/23.5 |
| 2005/0119761 | A1 |   | 6/2005 | Matsumoto |

FOREIGN PATENT DOCUMENTS

| JP | 3-065579 | 3/1991 |
| JP | 2597355 | 1/1997 |
| JP | 2000-302567 | 10/2000 |
| JP | 2002-179478 | 6/2002 |
| JP | 2003-073182 | 3/2003 |
| WO | 01/54747 | 8/2001 |

OTHER PUBLICATIONS

English Language Abstract of JP 3-065579.
English Language Abstract of JP 2003-073182.

* cited by examiner

*Primary Examiner*—Hai Vo
(74) *Attorney, Agent, or Firm*—Greenblum & Bernstein, P.L.C.

(57) ABSTRACT

A porous calcium phosphate ceramic body comprising a substrate 1, and three-dimensional nanotunnel layers 2 formed on wall surfaces of the substrate 1, the three-dimensional nanotunnel layers 2 having pluralities of three-dimensionally connected nanotunnels 21.

7 Claims, 3 Drawing Sheets

POROUS CALCIUM PHOSPHATE CERAMIC AND METHOD FOR PRODUCING SAME

FIELD OF THE INVENTION

The present invention relates to a porous calcium phosphate ceramic body excellent in biocompatibility and suitable for a carrier for the cultivation of cells or biological tissues and for biomaterials such as artificial dental roots and bone-filling materials, and a method for producing such a porous calcium phosphate ceramic body.

BACKGROUND OF THE INVENTION

Materials used for artificial bones, artificial dental roots, bone fillers, etc. (hereinafter referred to as "bone-filling materials") in dentistry, brain surgery, plastic surgery, orthopedic surgery, etc. are desired to have (a) no toxicity, (b) sufficient mechanical strength and (c) excellent compatibility with biological tissues.

Because porous calcium phosphate ceramics meet these conditions, they are utilized as bone-filling materials. When used as bone-filling materials, the porous calcium phosphate ceramics preferably have as high porosity as possible from the aspect of biocompatibility. However, because higher porosity leads to lower mechanical strength in the porous bodies, they cannot be used as bone-filling materials for portions needing high mechanical strength. Thus, porous calcium phosphate ceramics having both excellent biocompatibility and mechanical strength are desired.

JP 2000-302567 A (corresponding to U.S. Pat. No. 6,340,648) discloses a sintered body comprising a skeleton portion formed by substantially dense sintered calcium phosphate, which has a finely ragged surface or a porous sintered calcium phosphate layer on the surface. JP 2000-302567 A (corresponding to U.S. Pat. No. 6,340,648) describes that fine raggedness or a porous sintered calcium phosphate layer on the surface of the porous sintered body increases a specific surface area, making it easy for osteoblasts to attach to the surface of the porous sintered body.

However, research by the inventors has revealed that to accelerate the formation of new bone, bone-filling materials should be able to trap bone-forming proteins and act as a scaffold for osteoblasts, and that it is effective for that purpose that the bone-filling materials have nanometer-order fine pores with complicated structure on the surface. Even though there are fine projections and recesses on the surface as in the sintered calcium phosphate body of JP2000-302567 A (corresponding to U.S. Pat. No. 6,340,648), such surface fails to trap bone-forming proteins sufficiently to form new bone and does not act as a scaffold for osteoblasts. It has been found that the diameters of fine pores necessary for trapping bone-forming proteins and acting as a scaffold for osteoblasts are 1 to 5000 nm. In general, sintered porous calcium phosphate does not have fine pores with completed structure, whose diameters are more than 5000 nm. Accordingly, even though there are sintered porous calcium phosphate layers on the surface as in the sintered body of JP2000-302567 A (corresponding to U.S. Pat. No. 6,340,648), the formation of new bone cannot be sufficiently accelerated.

OBJECT OF THE INVENTION

Accordingly, an object of the present invention is to provide a porous calcium phosphate ceramic body having excellent new-bone-forming capability and large mechanical strength, and its production method.

DISCLOSURE OF THE INVENTION

As a result of intensive research in view of the above object, the inventors have found that (a) a porous calcium phosphate ceramic body comprising a calcium phosphate substrate and three-dimensional nanotunnel layers formed on the wall surfaces of the substrate, the nanotunnels being three-dimensionally connected, has excellent capability of forming new bone and large mechanical strength, and that (b) this porous calcium phosphate ceramic body is obtained by immersing the substrate in a slurry containing fine calcium phosphate particles, defoaming the slurry under reduced pressure, and drying and heat-treating the slurry-carrying substrate. The present invention has been completed based on such findings.

Thus, the porous calcium phosphate ceramic body of the present invention comprises a substrate, and three-dimensional nanotunnel layers formed on wall surfaces of the substrate and having pluralities of three-dimensionally connected nanotunnels.

The substrate preferably has fine pores, and the porosity of the substrate is preferably 40 to 98%. The substrate is preferably made of calcium phosphate.

The three-dimensional nanotunnel layers preferably have an average thickness of 20 nm to 10 μm. The three-dimensional nanotunnel layers are preferably formed on 5 to 100% of the wall surfaces of the fine pores. The nanotunnels preferably have openings communicating with the fine pores of the substrate, and at least part of the openings are preferably communicating with the fine pores of the substrate. The openings preferably have an average diameter of 1 to 5000 nm. The atomic ratio of Ca/P in the three-dimensional nanotunnel layers is preferably substantially equal to or smaller than that in the substrate.

The method of the present invention for producing a porous calcium phosphate ceramic body having three-dimensional nanotunnel layers comprises the steps of immersing a calcium phosphate substrate in a slurry containing fine calcium phosphate particles, defoaming the slurry under reduced pressure, and heat-treating the slurry-carrying substrate.

It is preferable to use fine calcium phosphate particles having an average diameter of 10 nm to 5 μm. The fine calcium phosphate particles preferably are as long as 10 to 200 nm in the c-axis and 1 to 100 nm in the a-axis, and have a specific surface area of 30 to 300 m$^2$/g. They are preferably calcium phosphate single crystals. The substrate is preferably porous, and the slurry containing fine calcium phosphate particles preferably enter into the fine pores.

The heat treatment is conducted preferably at a temperature of 600 to 900° C.

DESCRIPTION OF THE BEST MODE OF THE INVENTION

[1] Porous Calcium Phosphate Ceramic (1) Structure

Figure 1:
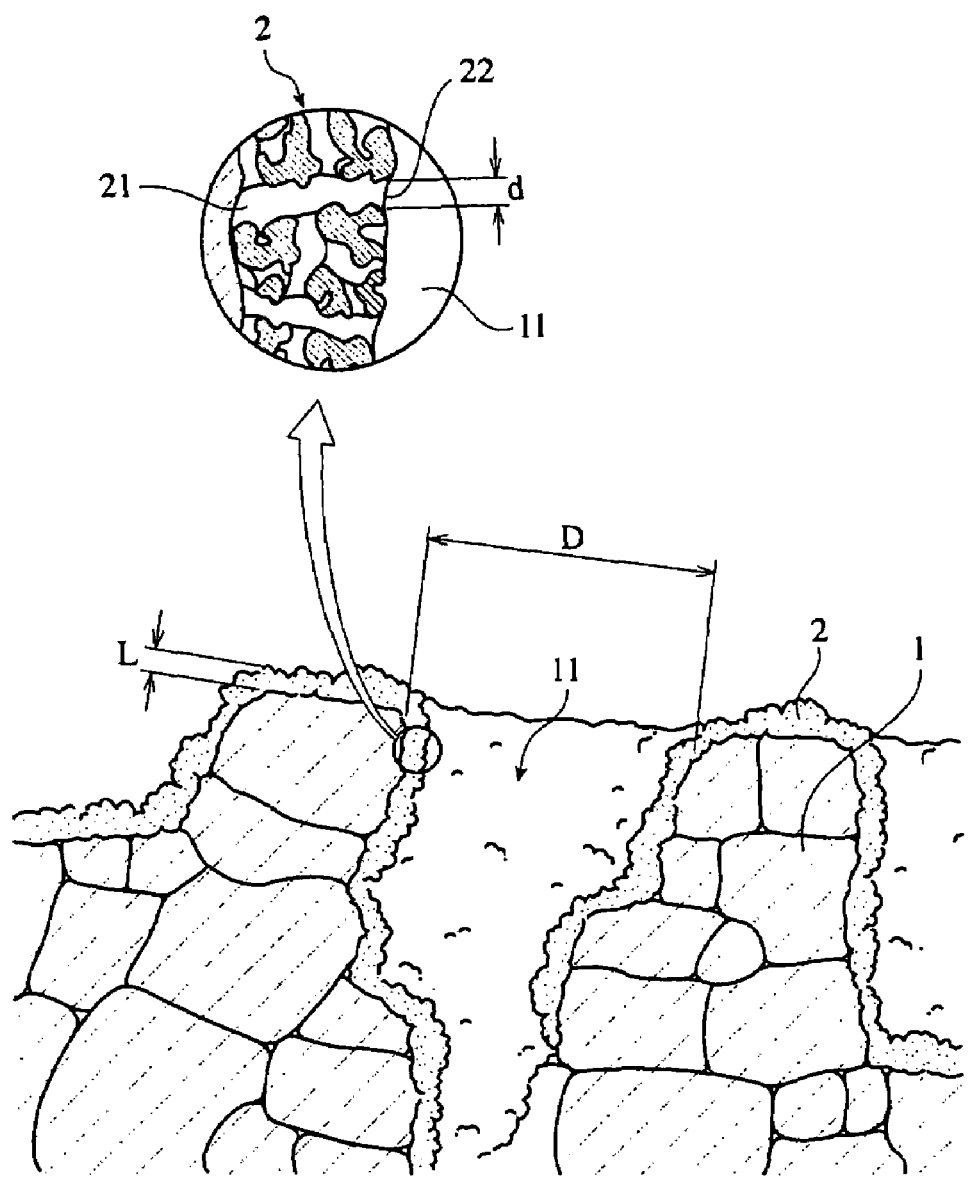
FIG. 1 is a cross-sectional view schematically showing the porous calcium phosphate ceramic body of the present invention.

FIG. 1 schematically shows a cross section of the porous calcium phosphate ceramic body. As shown in FIG. 1, the porous calcium phosphate ceramic body comprises a substrate 1, and three-dimensional nanotunnel layers 2 formed on wall surfaces of the substrate 1. Such porous calcium phosphate ceramic body comprising the substrate 1 and the three-dimensional nanotunnel layers 2 can be produced by the later-described method of the present invention.

Although the substrate 1 may be a porous or dense body, it is preferably a porous body. When the substrate 1 is porous, the three-dimensional nanotunnel layers 2 are formed in its fine pores 11, resulting in a porous calcium phosphate ceramic body with excellent biocompatibility and bone-forming capability. When the substrate 1 is porous, the fine pores 11 preferably have diameters D of about 50 to 500 µm. When the fine pores 11 have diameters D of less than 50 µm, osteoblasts cannot easily enter into the fine pores 11, resulting in difficulty in forming bone in the fine pores 11. When the diameter D exceeds 500 µm, the porous calcium phosphate ceramic body has too small mechanical strength. Though the skeleton portion of the substrate 1 may be porous or dense, it is preferably dense from the aspect of mechanical strength.

The porosity of the substrate 1 is preferably 40 to 98%, more preferably 60 to 90%. When the substrate 1 has a porosity of less than 40%, too small numbers of fine pores 11 are formed in the substrate 1, resulting in too few three-dimensional nanotunnel layers 2 formed in the fine pores 11. When the porosity is more than 98%, the porous calcium phosphate ceramic body has too small mechanical strength.

The average thickness L of the three-dimensional nanotunnel layers 2 is preferably 20 nm to 10 µm, more preferably 50 to 300 nm. The average thickness L can be determined from their scanning electron photomicrograph (SEM photograph) or their SEM image. When the average thickness L of the three-dimensional nanotunnel layers 2 is less than 20 nm, sufficient effect of providing the three-dimensional nanotunnel layers 2 with improved bone-forming capability cannot be obtained. When the average thickness L is more than 10 µm, the porous calcium phosphate ceramic body has undesirably small mechanical strength. The three-dimensional nanotunnel layers 2 are formed on preferably 5 to 100%, more preferably 10 to 70%, of the wall surfaces of the fine pores 11. Because the three-dimensional nanotunnel layers 2 are extremely light in weight, the mass ratio of the three-dimensional nanotunnel layers 2 to the porous calcium phosphate ceramic body is negligibly small, for instance, 0.001 to 0.05.

As shown in the partial enlarged view of FIG. 1, the three-dimensional nanotunnel layers 2 have pluralities of nanotunnels 21. The term "nanotunnels 21" used herein means fine pores having nanometer-level diameters. Because each nanotunnel 21 has at least one connection with the other nanotunnel 21 without orientation, it forms complicated networks in the three-dimensional nanotunnel layers 2. Such structure of the nanotunnels 21 is called "three-dimensionally connected structure."

At least part of the nanotunnels 21 have openings 22 communicating with the surface of the porous calcium phosphate ceramic body or the fine pores 11 of the substrate 1. The openings 22 of the nanotunnels 21 have an average diameter d of preferably 1 to 5000 nm, more preferably 10 to 2000 nm. The average diameter d can be determined from the SEM photograph or image of the nanotunnels 21. When the average diameter d of the openings 22 is less than 1 nm, bone-forming proteins, bone materials, etc., cannot easily enter into the nanotunnels 21. When the average diameter d is more than 5000 nm, they do no have enough capability of trapping the bone-forming proteins, etc. that have entered into the nanotunnels 21.

When the porous calcium phosphate ceramic body is embedded in a living body, the nanotunnels 21 in the three-dimensional nanotunnel layers 2 are filled with a body fluid. Bone-forming proteins contained in the filled body fluid are trapped in the nanotunnels 21. Undifferentiated mesenchymal cells, from which osteoblasts are generated, are attached to the surface of the porous calcium phosphate ceramic body or the fine pores 11, with the three-dimensional nanotunnel layers 2 as a scaffold, so that they are differentiated to osteoblasts in the fine pores 11. Because the osteoblasts are as large as about several tens of micrometers, they cannot easily enter into the nanotunnels 21, but can enter into the fine pores 11 of the substrate 1. Receiving bone-forming proteins adsorbed to the three-dimensional nanotunnel layers 2, the osteoblasts can form bone. Accordingly, when coming into contact with the three-dimensional nanotunnel layers 2 containing the bone-forming proteins, the osteoblasts are put in a state of easily forming bone, thereby accelerating the formation of bone around the porous calcium phosphate ceramic body and/or in the fine pores of the substrate.

(2) Composition (a) Substrate

The atomic ratio of Ca/P is preferably 1.0 to 1.7 in calcium phosphate forming the substrate. With the atomic ratio of Ca/P outside this range, it is difficult to provide a calcium phosphate ceramic with a crystal structure. A preferred example of the calcium phosphate is hydroxyapatite.

(b) Three-Dimensional Nanotunnel Layers

The atomic ratio of Ca/P in the three-dimensional nanotunnel layers is preferably substantially equal to or smaller than that in the substrate. When the three-dimensional nanotunnel layers and the substrate have substantially the same atomic ratio of Ca/P, the porous calcium phosphate ceramic body is relatively stable even when embedded in a living body. The porous calcium phosphate ceramic body stable in a living body can act as a support for relatively long period of time. The term "substantially equal" in the atomic ratio of Ca/P substrate means that the atomic ratio of Ca/P in the three-dimensional nanotunnel layers is 95 to 105% of that in the substrate.

If different, the atomic ratio of Ca/P in the three-dimensional nanotunnel layers is preferably smaller than that in the substrate. With a smaller Ca/P atomic number ratio than that in the substrate, the porous calcium phosphate ceramic body is easily dissolved in a body fluid or eroded by cells.

[2] Production Method of Porous Calcium Phosphate Ceramic Body (1) Production of Substrate The production method of the porous calcium phosphate ceramic body will be explained, taking for example a case where a porous calcium phosphate substrate is used. The substrate may be produced by general methods. The production method of the substrate will be explained, taking for example a case where hydroxyapatite powder, a water-soluble high-molecular compound and a nonionic surfactant are used as starting materials. The hydroxyapatite powder is preferably secondary particles having an average diameter (secondary particle size) of 0.5 to 80 µm, which are composed of primary particles having an average diameter of 100 nm or less. The same starting materials are preferably used for the later-described slurry for the three-dimensional nanotunnel layers.

Examples of the water-soluble high-molecular compound include cellulose derivatives such as methylcellulose, carboxymethylcellulose, etc., polysaccharides such as curdlan, polyvinyl alcohol, polyacrylic acid, polyacrylamide, and polyvinyl pyrrolidone, etc, and methylcellulose is preferable among them. Examples of the nonionic surfactant include aliphatic acid alkanolamides, polyoxyethylene alkyl ether carboxylates, polyoxyethylene alkyl ethers (for instance, polyoxyethylene octylphenyl ether).

A slurry for the substrate containing the hydroxyapatite powder, the water-soluble high-molecular compound and the nonionic surfactant is prepared. The preferred composition of the slurry for the substrate comprises 100 parts by mass of hydroxyapatite powder, 1 to 10 parts by mass of the water-soluble high-molecular compound, and 1 to 10 parts by mass of the nonionic surfactant. The total concentration of the hydroxyapatite powder+the water-soluble high-molecular compound+the nonionic surfactant (the concentration of solid components in the slurry for the substrate) is preferably 20 to 50% by mass.

After the slurry for the substrate is foamed by stirring, it is heated at 80° C. or higher and lower than 100° C. When heated to 100° C. or higher, the slurry is boiled, resulting in disappearance of fine foams. The more preferred heating temperature is 80 to 90° C. When the slurry for the substrate is heated, gelation occurs by the action of the water-soluble high-molecular compound. The resultant gel is dried, cut and degreased, and then sintered at 1000 to 1200° C. to obtain a porous calcium phosphate body.

The production method of the porous calcium phosphate body is described in JP2002-179478 A, etc. in detail.

(2) Preparation of Slurry for Three-Dimensional Nanotunnels Layers

Fine calcium phosphate particles are mixed with water and stirred to form a slurry for the three-dimensional nanotunnel layers. The slurry for the three-dimensional nanotunnel layers is preferably single dispersion or near single dispersion. When the slurry is not in a single dispersion state or near a single dispersion state, the slurry contains large particles and small particles, failing to provide three-dimensional nanotunnel layers with uniform thickness and nanotunnel diameters.

To put the slurry in a single dispersion state or near a single dispersion state, it is preferable that (a) fine calcium phosphate particles with uniform particle sizes are used, that (b) the pH of the slurry is adjusted to 6.5 to 7.5, and that (c) a dispersant is added to the slurry. Of course, these methods (a) to (c) may be combined. Their specific examples are fine calcium phosphate particles, 50% of which (in the number) have particle sizes within a range of 10 to 100 nm. The dispersant is preferably removable in the later-described heat treatment step. Specific examples of the dispersant may be the same as the surfactants usable in the production of the above-described substrate.

The fine calcium phosphate particles may be single crystals or agglomerates, though their average diameter is preferably 10 nm to 5 μm. The fine calcium phosphate particles are as long as 10 to 200 nm in the c-axis and 1 to 100 nm in the a-axis. With the particle sizes of the fine calcium phosphate particles within these ranges, the three-dimensional nanotunnel layers are easily formed. The fine calcium phosphate particles with such size can be produced by general wet methods. The synthesis reaction may be uniform or non-uniform.

The specific surface area of the fine calcium phosphate particles is preferably 30 to 300 $m^2/g$, more preferably 50 to 200 $m^2/g$. When the specific surface area is less than 30 $m^2/g$, the fine calcium phosphate particles are too large to form the three-dimensional nanotunnel layers easily. The particles having a specific surface area exceeding 300 $m^2/g$ cannot be produced easily by presently available technologies. A uniform synthesis reaction provides the particles with a specific surface area of about 100 to 300 $m^2/g$, while a non-uniform synthesis reaction provides the particles with a specific surface area of about 30 to 100 $m^2/g$.

The concentration of solid components is preferably 0.1 to 5% by mass in the slurry for the three-dimensional nanotunnel layers. When the concentration of solid components is less than 0.1% by mass, three-dimensional nanotunnel layers having preferred thickness cannot be formed. When the concentration of solid components is more than 5% by mass, the fine particles tend to agglomerate. As a result, the fine particles are localized in fine pores on the surface without entering into fine pores inside the substrate, resulting in difficulty in forming the three-dimensional nanotunnel structure.

(3) Immersion of Substrate in Slurry for Three-Dimensional Nanotunnels Layer

The substrate is immersed in the slurry for the three-dimensional nanotunnel layers. It is preferable to immerse the substrate completely in the slurry for the three-dimensional nanotunnel layers. By defoaming the slurry under a reduced pressure in a state where the substrate is immersed in the slurry for the three-dimensional nanotunnel layers, fine calcium phosphate particles in the slurry are sufficiently attached to the wall surfaces of the substrate. Because the fine calcium phosphate particles in the slurry for the three-dimensional nanotunnel layers are sufficiently small, they enter into the fine pores of the substrate, so that they are attached to the wall surfaces of the substrate. Thus, by defoaming the slurry for the three-dimensional nanotunnel layers in a state where the substrate is immersed, the three-dimensional nanotunnel layers are formed on the wall surfaces of fine pores in the substrate.

The defoaming time under a reduced pressure is preferably about 3 to 15 minutes. When it is less than 3 minutes, the slurry does not sufficiently enter into the fine pores. Even if it exceeds 15 minutes, the three-dimensional nanotunnel layers would not increase.

(4) Drying

The porous calcium phosphate body provided with the three-dimensional nanotunnel layers is dried. The drying is preferably conducted at such a high temperature that water is not boiled (for instance, higher than 80° C. and lower than 100° C.). When water is boiled, cracking undesirably occurs in the three-dimensional nanotunnel layers.

(5) Heat Treatment

After the porous calcium phosphate body provided with the three-dimensional nanotunnel layers is dried, a heat treatment is conducted. The three-dimensional nanotunnel layers are bonded to the wall surfaces of the substrate by the heat treatment. The heat treatment temperature is preferably 600 to 900° C. When the heat treatment temperature is lower than 600° C., the three-dimensional nanotunnel layers are too much bonded to the substrate. The higher the heat treatment temperature, the stronger the bonding of the three-dimensional nanotunnel layers to the substrate. However, when the heat treatment temperature is higher than 900° C., calcium phosphate particles themselves are excessively fused to each other to become dense, thereby loosing the three-dimensional nanotunnels structure.

The present invention will be explained in more detail referring to Examples below without intention of restricting the scope of the present invention.

Example 1

(1) Production of Sintered Porous Hydroxyapatite Body

Hydroxyapatite was produced by a wet synthesis method, and granulated while drying by a spray drier. The resultant hydroxyapatite powder was calcined at 700° C. and pulverized. The hydroxyapatite powder had a specific surface area of 50 m$^2$/g. 120 parts by mass of the hydroxyapatite powder having an average diameter of 10 μm was introduced into 320 parts by mass of an aqueous solution of 1-%-by mass methylcellulose having a viscosity of 4000 cps (measured at 20° C. in a 2-%-by-mass aqueous solution) (available from Wako Pure Chemical Industries, Ltd.,), and 10 parts by mass (on a solid basis) of a fatty acid alkanolamide surfactant [N,N-dimethyldodecylamine oxide, "AROMOX" (trademark) available from Lion Corporation] was added. A slurry containing this hydroxyapatite powder, methylcellulose and the fatty acid alkanolamide surfactant was charged into a homogenizer (PA92 available from SMT Co., Ltd.). While keeping the temperature at 10° C., the slurry was vigorously stirred to be foamed for 5 minutes at an actual stirring force of 60 W/L.

The resultant foamed slurry was poured into a molding die, heated at 83° C. for 2 hours to cause gelation. The resultant gel was kept at 83° C. in the molding die to be completely dried.

The dried gel was cut to a cube of about 10 mm each, and heated from room temperature to 700° C. at a speed of 50° C./hour and then to 1200° C. at a speed of 100° C./hour in the air, and sintered at this temperature for 4 hours. Thereafter, it was cooled to 600° C. at a speed of 50° C./hour, kept at this temperature for 4 hours, and then cooled to room temperature at a speed of 100° C./hour to obtain a sintered hydroxyapatite body having a porosity of 85%. The sintered hydroxyapatite body was in a cubic shape of 10 mm each. The sintered hydroxyapatite body had a substantially dense skeleton portion.

(2) Porous Hydroxyapatite Ceramics

The same hydroxyapatite as used in the production of the sintered hydroxyapatite body in the step (1) of Example 1 was pulverized to fine particles having an average diameter of 80 nm. The resultant fine hydroxyapatite particles were as long as 50 to 100 nm in the c-axis and 10 to 50 nm in the a-axis, and had a specific surface area of 50 to 80 m$^2$/g. 1.0 g of the fine hydroxyapatite particles was added to water to a solid concentration of 2.0% by mass, and stirred to form an appetite slurry for three-dimensional nanotunnels layers. The sintered hydroxyapatite body was immersed in this appetite slurry, and defoamed for 5 minutes under reduced pressure.

Figure 2:
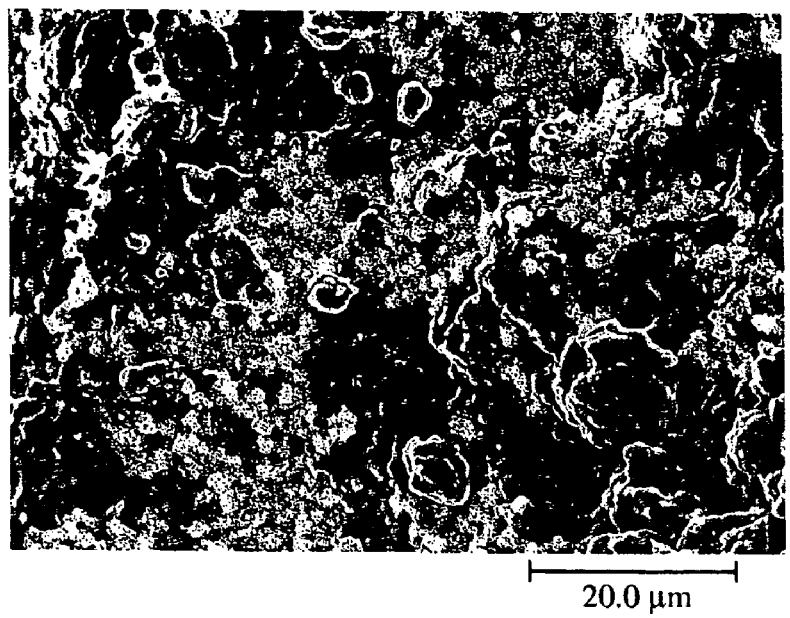
FIG. 2 is a SEM photomicrograph of the porous calcium phosphate ceramic body of Example 1.
Figure 3:
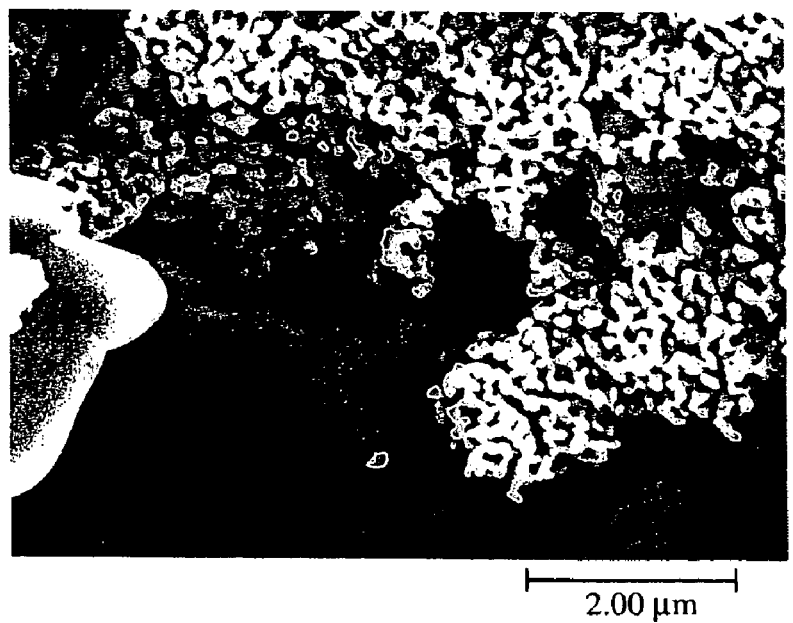
FIG. 3 is another SEM photomicrograph of the porous calcium phosphate ceramic body of Example 1.

The sintered hydroxyapatite body carrying the appetite slurry was heat-treated at 700° C. for 4 hours, and cooled to near room temperature at a speed of 50° C./hour. The resultant porous hydroxyapatite ceramic body had a porosity of 85%. There was substantially no difference in the measured porosity of the sintered hydroxyapatite body between before and after attaching the slurry. This appears to be due to the fact that the percentage of nanotunnel layers occupying the sintered hydroxyapatite body was extremely small. FIGS. 2 and 3 are the scanning electron photomicrographs (SEM photographs) of the porous hydroxyapatite ceramic body. The three-dimensional nanotunnel layers were formed on about 10% of the surfaces of the sintered hydroxyapatite substrate. The three-dimensional nanotunnel layers had an average thickness of about 300 nm, with openings having diameters of about 10 to 200 nm.

Comparative Example 1

Figure 4:
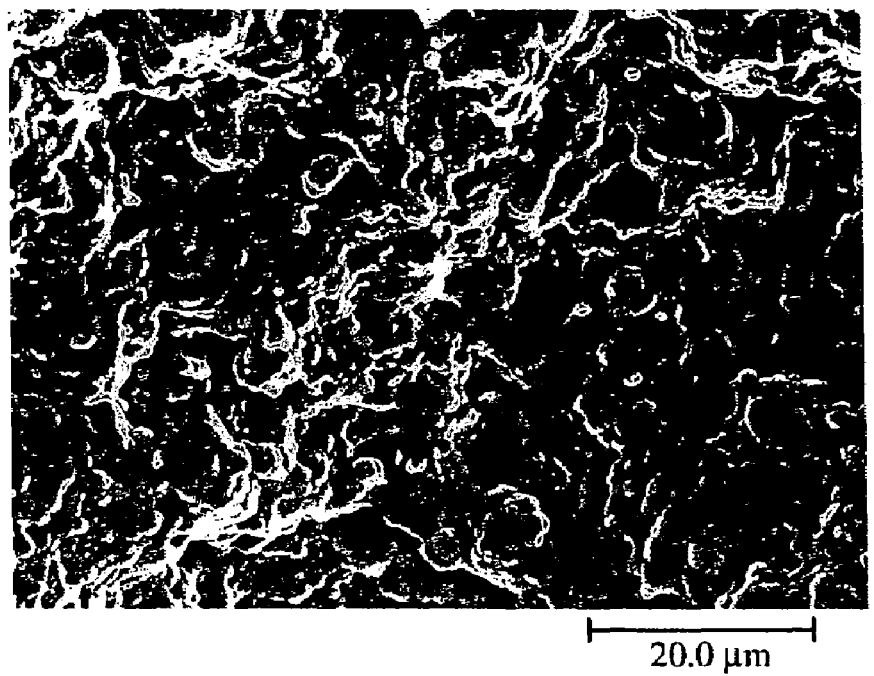
FIG. 4 is a SEM photomicrograph of the sintered hydroxyapatite body of Comparative Example 1.

The SEM photograph of the sintered hydroxyapatite body produced in the step (1) of Example 1 is shown in FIG. 4. It is clear from the SEM photograph that three-dimensional nanotunnel layers were not formed on the surface of the sintered hydroxyapatite body of Comparative Example 1.

EFFECT OF THE INVENTION

The porous calcium phosphate ceramic body of the present invention has three-dimensional nanotunnel layers on wall surfaces of the substrate, and the three-dimensional nanotunnel layers have pluralities of nanotunnels. The nanotunnels are three-dimensionally connected. Bone-forming proteins and osteoblasts can enter into the nanotunnels. Accordingly, bone is easily formed on the porous calcium phosphate ceramic body and/or in fine pores thereof. Because the substrate has a relatively dense structure, the porous calcium phosphate ceramic body has sufficient mechanical strength. Such porous calcium phosphate ceramic body having excellent bone-forming capability and mechanical strength is suitable as a bone-filling material. The porous calcium phosphate ceramic body comprising a substrate and three-dimensional nanotunnel layers can be easily produced by the method of the present invention, which comprises immersing the substrate in a slurry containing calcium phosphate particles, defoaming it under reduced pressure, and heat-treating the slurry-carrying substrate.

The present disclosure relates to subject matter contained in Japanese Patent Application No. 2003-366404 (filed on Oct. 27, 2003), which is expressly incorporated herein by reference in its entirety.

What is claimed is:

1. A porous calcium phosphate ceramic body comprising a substrate having fine pores, and three-dimensional nanotunnel layers having pluralities of three-dimensionally connected nanotunnels formed on wall surfaces of said fine pores by mixing together calcium phosphate particles, a dispersant and water to form a slurry in a single dispersion state or near a single dispersion state, immersing said substrate in said slurry, and defoaming said slurry under reduced pressure, wherein said three-dimensional nanotunnel layers are formed in the fine pores inside the substrate, wherein a thickness of said three-dimensional nanotunnel layers is from 20 to 300 nm, wherein at least part of said nanotunnels have openings communicating with the fine pores of said substrate and said openings have an average diameter of 1 to 200 nm, and wherein the substrate and the three-dimensional nanotunnel layers are made from calcium phosphate.

2. The porous calcium phosphate ceramic body according to claim 1, wherein said three-dimensional nanotunnel layers are formed on 5 to 100% of the wall surfaces of said fine pores.

3. The porous calcium phosphate ceramic body according to claim 1, wherein said substrate has a porosity of 40 to 98%.

4. The porous calcium phosphate ceramic body according to claim 1, wherein an atomic ratio of Ca/P in said three-dimensional nanotunnel layers is substantially equal to or smaller than that in said substrate.

5. The porous calcium phosphate ceramic body according to claim 1, wherein the pores of the substrate have diameters of about 50 to 500 μm.

6. The porous calcium phosphate ceramic body according to claim 1, wherein said dispersant is a nonionic surfactant.

7. A porous calcium phosphate ceramic body comprising a substrate having fine pores, and three-dimensional nanotunnel layers having pluralities of three-dimensionally connected nanotunnels formed on wall surfaces of said fine pores, wherein the three-dimensional nanotunnel layers are produced by a method comprising:

mixing together calcium phosphate particles, a dispersant and water to form a slurry in a single dispersion state or near a single dispersion state;

immersing the substrate in the slurry;

defoaming the slurry under reduced pressure;

drying the porous calcium phosphate ceramic body at a temperature below a boiling point of water, followed by a heat treatment at a temperature between 600 to 900° C.;

wherein the three-dimensional nanotunnel layers are formed in the fine pores inside the substrate;

a thickness of said three-dimensional nanotunnel layers is from 20 to 300 nm;

at least part of said nanotunnels have openings communicating with the fine pores of said substrate and said openings have an average diameter of 1 to 200 nm;

the three-dimensional nanotunnel layers are from on 5 to 70% of the wall surface of said fine pores;

a mass ratio of the three-dimensional nanotunnel layers to the ceramic body is from 0.001 to 0.05; and the substrate and three-dimensional nanotunnel layers are made from calcium phosphate.

* * * * *